United States Patent
Xu et al.

(10) Patent No.: US 12,140,584 B1
(45) Date of Patent: Nov. 12, 2024

(54) METHODS FOR EVALUATING PRODUCTION POTENTIAL FOR VOLUME FRATURING OF SHALE OIL RESERVOIRS AND DETERMING SOAKING TIMES

(71) Applicant: YANGTZE UNIVERSITY, Hubei (CN)

(72) Inventors: Wenjun Xu, Wuhan (CN); Feng Jiang, Wuhan (CN); Jianpeng Zhang, Wuhan (CN); Lei Wang, Wuhan (CN); Yuanai Liao, Wuhan (CN)

(73) Assignee: YANGTZE UNIVERSITY (CN)

( * ) Notice: Subject to any disclaimer, the term of this patent is extended or adjusted under 35 U.S.C. 154(b) by 0 days.

(21) Appl. No.: 18/735,165

(22) Filed: Jun. 5, 2024

(30) Foreign Application Priority Data

Nov. 1, 2023 (CN) .......................... 202311456279.X

(51) Int. Cl.
*G01N 33/24* (2006.01)
*G01N 15/08* (2006.01)

(52) U.S. Cl.
CPC ........... *G01N 33/241* (2013.01); *G01N 15/08* (2013.01)

(58) Field of Classification Search
CPC .............................. G01N 15/08; G01N 33/241
USPC ........................................ 73/152.09, 152.11
See application file for complete search history.

(56) References Cited

U.S. PATENT DOCUMENTS

| | | | | |
|---|---|---|---|---|
| 5,335,724 A | * | 8/1994 | Venditto | E21B 43/26 166/250.1 |
| 9,063,247 B2 | * | 6/2015 | Li | G01V 1/30 |
| 10,571,605 B2 | * | 2/2020 | Crawford | G01V 20/00 |
| 11,112,373 B1 | * | 9/2021 | AlSinan | G01N 24/081 |
| 11,143,607 B2 | * | 10/2021 | Elsayed | G01R 33/46 |

(Continued)

FOREIGN PATENT DOCUMENTS

| | | | | |
|---|---|---|---|---|
| CN | 109883922 A | | 6/2019 | |
| CN | 110441204 A | * | 11/2019 | G01N 15/08 |

(Continued)

OTHER PUBLICATIONS

Sun et al. "Experimental and Numerical Studies of CO2 EOR in Unconventional Liquid Reservoirs with Complex Fracture Networks" Society of Petroleum Engineers, SPE-179634-MS (Year: 2016).*

(Continued)

*Primary Examiner* — John Fitzgerald

(57) ABSTRACT

A method for evaluating a production potential for volume fracturing of a shale oil reservoir and determining a soaking time is discloses. The method may comprise: obtaining a core column; performing a saturated oil treatment on the core column; obtaining an initial fracture porosity parameter of the saturated oil-treated core column; soaking the core column after a CT scanning into a fracturing fluid to test the core mass increase amount at different immersion durations; obtaining the fracture porosity increase amount of the core column at different soaking times, and calculating a weight of newly added fracture porosity-fillable fracturing fluid; generating a curve of the core mass increase amount and a curve of the weight of the newly added fracture porosity-fillable fracturing fluid at different immersion durations; comparing a mass increase amount per volume unit of a core, and ranking a e mass increase amount per volume unit of the core to determine the production increase potential.

4 Claims, 5 Drawing Sheets

(56) References Cited

U.S. PATENT DOCUMENTS

| | | | |
|---|---|---|---|
| 11,313,211 B2* | 4/2022 | Johnson | E21B 47/06 |
| 11,867,047 B2* | 1/2024 | Han | E21B 43/267 |
| 2021/0003727 A1 | 1/2021 | Zhu et al. | |

FOREIGN PATENT DOCUMENTS

| | | | |
|---|---|---|---|
| CN | 111948109 A | 11/2020 | |
| CN | 112112622 A | 12/2020 | |
| CN | 112177608 A | 1/2021 | |
| CN | 115263286 A | 11/2022 | |
| CN | 115713049 A | 2/2023 | |
| CN | 115788402 A | 3/2023 | |

OTHER PUBLICATIONS

Juri et al. "Enhanced Oil Recovery in Vaca Muerta Shale-Oil Could Kick Production with Good Economics" Unconventional Resources Technology Conference, URTeC:1491 (Year: 2020).*

Li, Yang et al., Study on Shut-in Technology After Horizontal Well Fracturing, Liaoning chemical industry, 49(7):794-796, 2020.

Huang, Youquan et al., Analysis of factors influencing fracturing energization in tight oll reservoirs in Daqing Oilfield, Oil Drilling & Production Technology, 44(5): 611-617, 2022.

First Office Action in Chinese Application No. 202311456279.X mailed on Mar. 7, 2024, 17 pages.

Notification to Grant Patent Right for Invention in Chinese Application No. 202311456279.X mailed on Apr. 12, 2024, 4 pages.

\* cited by examiner

METHODS FOR EVALUATING PRODUCTION POTENTIAL FOR VOLUME FRATURING OF SHALE OIL RESERVOIRS AND DETERMING SOAKING TIMES

CROSS-REFERENCE TO RELATED APPLICATIONS

This application claims priority to Chinese Patent Application No. 202311456279.X, filed on Nov. 1, 2023, the entire contents of which are hereby incorporated by reference.

TECHNICAL FIELD

The present disclosure relates to the field of oil and gas field development engineering technology, and particularly to a method for evaluating a production potential for volume fracturing of a shale oil reservoir and determining a soaking time.

BACKGROUND

Volume fracturing is a key technology to realize efficient development of shale reservoirs. The practical engineering shows that a proper soaking after volume fracturing of a shale oil reservoir is conducive to increasing oil well production. However, the current determination of soaking time is mainly based on engineering experience, which lacks theoretical basis. Too short soaking time may result in poor stimulation effect, while too long soaking time may cause serious damage to the reservoir. Therefore, determining an optimal soaking time is of great significance for the efficient development of shale oil reservoirs.

Currently, a commonly used process for determining the soaking time is obtained based on the soaking time and production data of fractured shale oil wells in a target block. However, due to the strong heterogeneity of shale oil reservoirs and the large differences in reservoir features among wells, even adjacent wells have weak data correlation. Another commonly used process is shale hydration experiments, which can determine the optimal soaking time based on the effect of hydration-induced permeability enhancement. However, the mechanism of soaking to increase production in shale oil reservoirs is exceptionally complex, requiring comprehensive consideration of multiple factors such as hydration-induced permeability enhancement and oil-water displacement.

In addition, for shale oil reservoirs developed using horizontal well volume fracturing, a horizontal well section, which can be several kilometers long, may penetrate multiple shale oil reservoirs simultaneously. How to effectively evaluate a production potential of reservoirs at different positions along the horizontal well section has long been a difficult problem for technicians in this field.

In summary, there is an urgent need to develop a simple and efficient method for evaluating the production potential for volume fracturing of a shale oil reservoir and determining a soaking time after fracturing.

SUMMARY

One or more embodiments of the present disclosure provide a method for evaluating a production potential for volume fracturing of a shale oil reservoir and determining a soaking time, comprising: S1, obtaining a core of a target reservoir, cleaning the core and processing the core into a core column, wherein two end surfaces of the core column are kept flat; S2, performing a saturated oil treatment on the core column at a temperature of the target reservoir and a pressure condition of the target reservoir; S3, performing a CT scanning experiment on the core column after the saturated oil treatment, and obtaining an initial fracture porosity parameter of the core column combined with a digital core technology; S4, immersing the core column after the CT scanning experiment into fracturing fluid at the temperature of the target reservoir and the pressure condition of the target reservoir, and testing a core mass increase amount of the core column at different immersion durations; S5, performing the CT scanning experiment again on the core column immersed at different immersion durations, respectively, obtaining an increased amount of fracture porosity at different immersion durations combined within the digital core technology and the initial fracture porosity parameter, and calculating a weight of newly added fracture porosity-fillable fracturing fluid at different immersion durations; S6, generating a curve of the core mass increase amount and a curve of the weight of the newly added fracture porosity-fillable fracturing fluid at different immersion durations, and designating an immersion time corresponding to an intersection of the two curves as an optimal soaking time; S7, performing the operations S1-S6 on cores of a plurality of shale oil reservoirs to be evaluated for the production potential, respectively, comparing a mass increase amount per volume unit of a core corresponding to the optimal soaking time for the cores in the operation S6, and ranking a mass increase amount per volume unit of the core to determine the production potential corresponding to each of the plurality of shale oil reservoirs; wherein in the operation S2, a vacuum treatment is performed on the core column, a duration of the vacuum treatment is not less than 48 h, a temperature and a pressure condition of the saturated oil is the same as the temperature and the pressure condition of the target reservoir during the saturated oil treatment, and for ensuring that an intermediate vessel is completely filled with the saturated oil, the duration of the saturated oil treatment is not less than 48 h; in the operation S5, an equation for calculating the weight of the newly added fracture porosity-fillable fracturing fluid is as follow:

$$\Delta m_{nf} = \Delta \Phi \times V \times \rho$$

wherein $\Delta m_{nf}$ refers to the weight of the newly added fracture porosity-fillable fracturing fluid, unit in g; $\Delta \Phi$ refers to an increased amount of fracture porosity, unit in %; V refers to a total volume of the core column, unit in cm$^3$; $\rho$ refers to a density of the fracturing fluid, unit in g/cm$^3$;

in the operation S7, the greater the mass increase amount per volume unit of the core corresponding to the optimal soaking time is, the greater the increase in the production potential of the target reservoir corresponding to the core is, a calculation equation is as follow:

$$\eta = \frac{\Delta m}{V}$$

wherein $\eta$ refers to the mass increase amount per volume unit of the core corresponding to the optimal soaking time, unit in g/cm$^3$; $\Delta m$ refers to a cumulative increase in weight of the core corresponding to the optimal soaking time, unit in g.

In some embodiments, in the operation S1, the core column is a standard column, upper and lower end surfaces of the core column are kept flat, the method further includes: numbering the core column and recording a dimension, a weight, and a volumetric parameter of the core column.

In some embodiments, the method further includes: in the operation S3, obtaining the initial fracture porosity based on the CT scanning experiment and the digital core technology.

In some embodiments, in the operation S4, a rubber sleeve with high-temperature- and high-pressure-resistant is configured to wrap a side surface of the core column, and a circular interface at two ends of the core column are retained in contact with the fracturing fluid to prevent a prolonged high temperature and high pressure immersion causing the core column to break up and fall apart.

BRIEF DESCRIPTION OF THE DRAWINGS

This description will be further explained in the form of exemplary embodiments, which will be described in detail by means of accompanying drawings. These embodiments are not restrictive, in which the same numbering indicates the same structure, wherein.

DETAILED DESCRIPTION

Figure 1:
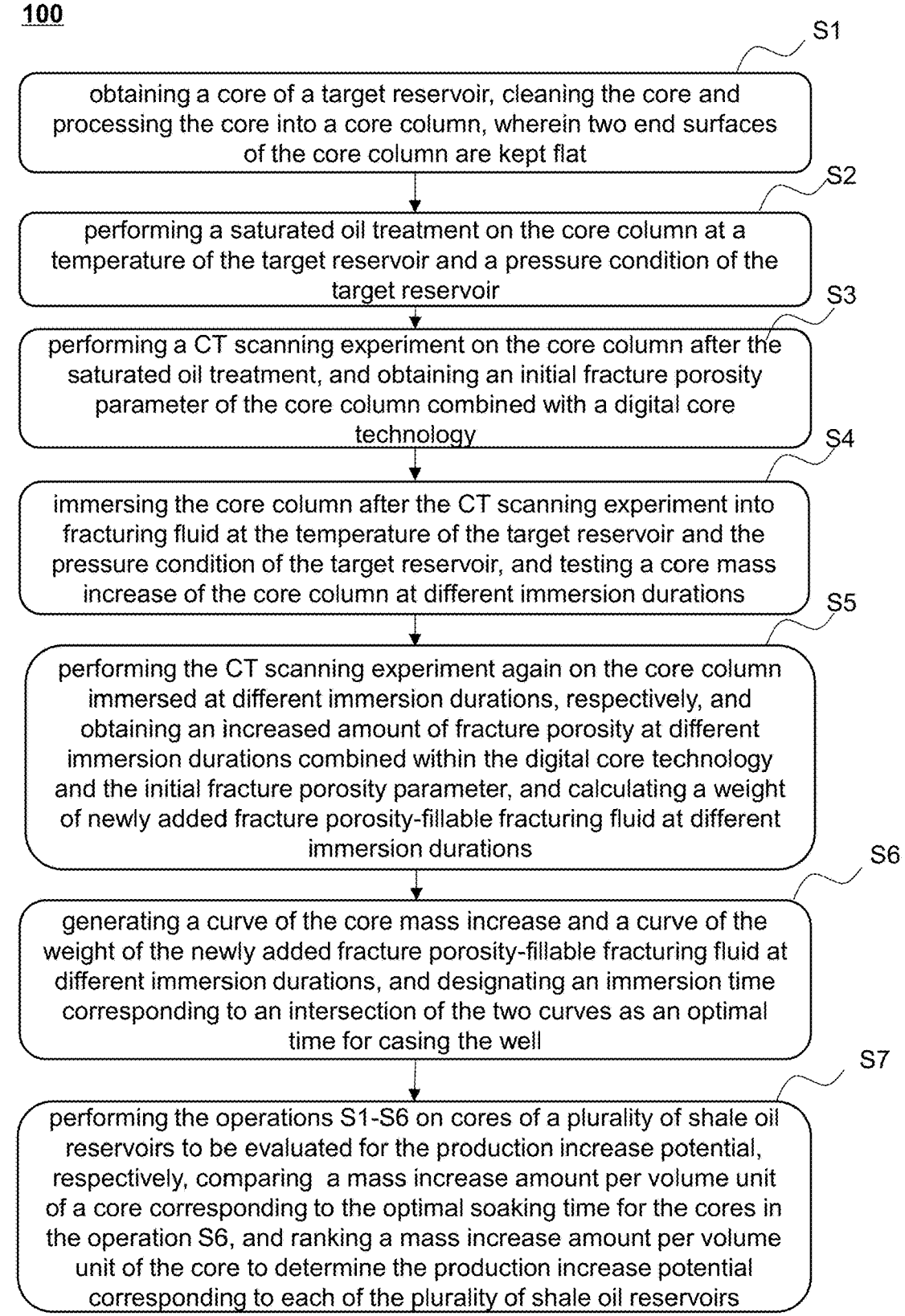
FIG. 1 is an exemplary flowchart illustrating a process for evaluating a production potential for volume fracturing of a shale oil reservoir and determining a soaking time according to some embodiments of the present disclosure.

In the following detailed description, numerous specific details are set forth by way of examples in order to provide a thorough understanding of the relevant disclosure. Obviously, drawings described below are only some examples or embodiments of the present disclosure. Those skilled in the art, without further creative efforts, may apply the present disclosure to other similar scenarios according to these drawings. Unless obviously obtained from the context or the context illustrates otherwise, the same numeral in the drawings refers to the same structure or operation.

It will be understood that the terms "system," "device," "unit," and/or "module" used herein are one method to distinguish different components, elements, parts, sections, or assemblies of different levels. However, the terms may be displaced by another expression if they achieve the same purpose.

As shown in the present disclosure and the claims, unless the context clearly suggests an exception, the words "one," "a", "an", and "the" do not refer specifically to the singular, but may also include the plural. Generally, the terms "including" and "comprising" suggest only the inclusion of clearly identified steps and elements. In general, the terms "including" and "comprising" only suggest the inclusion of explicitly identified steps and elements that do not constitute an exclusive list, and the method or device may also include other steps or elements.

In some embodiments, a system for evaluating a production potential for volume fracturing of a shale oil reservoir and determining a soaking time (hereinafter referred to as the "system") may be used to evaluate the production potential for volume fracturing of the shale oil reservoir and determining the soaking time.

In some embodiments, the system may control various functional devices to achieve corresponding functional processing. For example, the system may control a mechanical device for processing ae core. As another example, the system may soak a core column through an intermediate vessel.

In some embodiments, the system may communicate and connect with various functional devices to achieve corresponding functional processing. For example, the system may be communicatively connected with a computed tomography (CT) scanning device to perform a CT scanning experiment on the core column. In some embodiments, the system may include a processor that may further process results obtained from the functional devices' processing (e.g., plotting, sorting, etc.) to obtain relevant parameters or graphs in order to evaluate the production potential and determine the soaking time.

FIG. 1 is an exemplary flowchart illustrating a process for evaluating a production potential for volume fracturing of a shale oil reservoir and determining a soaking time according to some embodiments of the present disclosure. As shown in FIG. 1, a process 100 includes the following operations. In some embodiments, the process 100 may be performed by a system.

In S1, a core of a target reservoir may be obtained, the core may be cleaned and the core may be processed into a core column, wherein two end surfaces of the core column are kept flat.

The target reservoir is a shale oil reservoir for which the production potential and the soaking time are to be determined. The core is a rock sample taken from a borehole in the target reservoir using a ring-shaped core drill bit and other coring tools, according to the needs of geological exploration work or projects. The rock sample is usually cylindrical and may also be called a core column. The core column may be further processed into a regular cylindrical shape according to experimental needs.

Through the core, it is possible to understand an age, lithology, and sedimentary characteristics of a stratum; physical and chemical properties of the reservoir, oil, gas, and water content; characteristics and indicators of an oil-generating layer; underground structural conditions (e.g., faults, joints, dips, etc.); basic data for qualitative and quantitative interpretation of various logging methods; and parameters such as the movement and distribution of oil, gas, and water during the mining process, and changes in stratum structure.

In some embodiments, the system may estimate oil reserves, formulate reasonable development plans, and improve an efficiency of waterflood development and recovery ratio of the reservoir through experimental analysis of the core column.

In some embodiments, the core column is a standard cylinder, wherein upper and lower surfaces are kept flat. The system may number the core columns and record a dimension, a weight, volume parameters, etc. of each core column.

By adopting the standard cylinder, the standardization of the experimental basis is ensured, thus improving the accuracy of experimental results.

In S2, a saturated oil treatment may be performed on the core column at a temperature of the target reservoir and a pressure condition of the target reservoir.

In some embodiments, in operation S2, a vacuum treatment is performed on the core column, a duration of the vacuum treatment is not less than 48 h. A temperature and pressure condition of a saturated oil (also known as a crude oil) may be the same as a temperature and pressure condition of the target reservoir, at the same time, it should be ensured that an intermediate vessel is completely filled with saturated oil, and the saturation time is not less than 48 hours.

In some embodiments, the core column may perform a saturated oil treatment through an experimental equipment. In some embodiments, the experimental equipment may be communicatively connected to a processor of the system, and the processor may send control instructions to the experimental equipment to control the experimental equipment.

Figure 2:
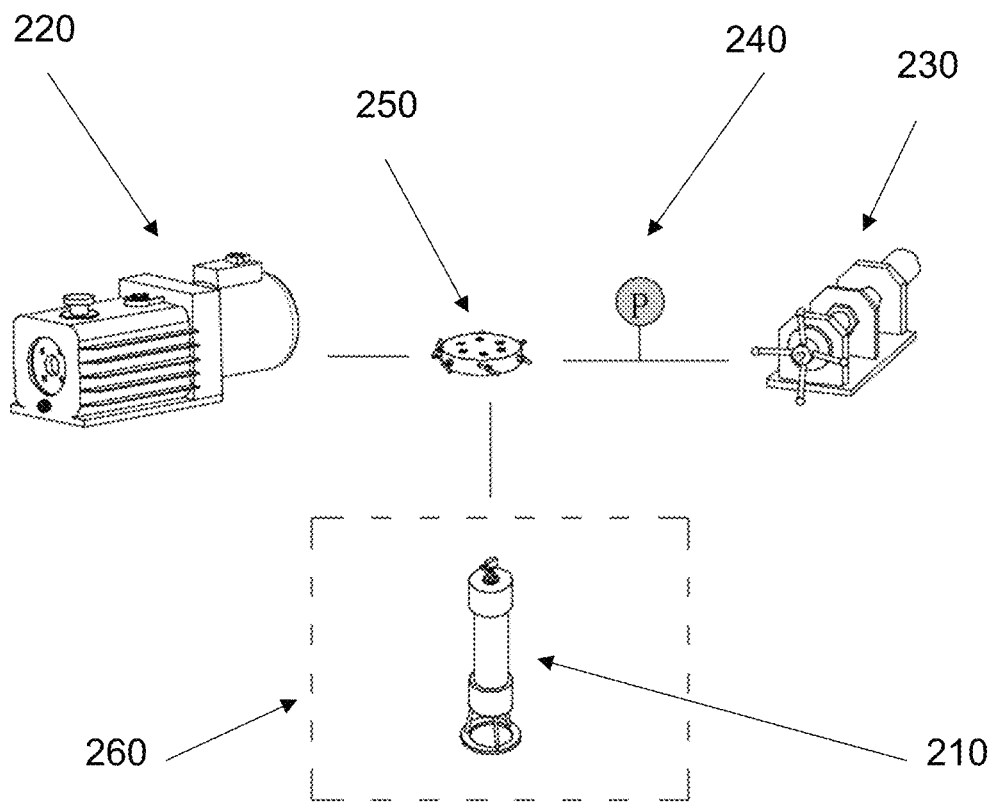
FIG. 2 is a schematic diagram illustrating an experimental equipment according to some embodiments of the present disclosure.

FIG. 2 is a schematic diagram illustrating an experimental equipment according to some embodiments of the present disclosure.

Before illustrating the saturated oil treatment process, the following may illustrate the experimental equipment as shown in FIG. 2. It should be understood that the experimental equipment shown in FIG. 2 is only an example, and that the saturated oil treatment may be performed on the core column by other feasible equipment.

In some embodiments, as shown in FIG. 2, the experimental equipment may include an intermediate vessel 210, and functional devices (e.g., a vacuum pump 220, a pressure pump 230, etc.) in communication with the intermediate vessel 210.

The intermediate vessel 210 is configured to accommodate the core column and provide experimental conditions to the core column.

In some embodiments, the intermediate vessel 210 may be connected to the vacuum pump 220, thereby vacuuming the intermediate vessel 210.

In some embodiments, the intermediate vessel 210 may be connected to a pressure pump 230, which enables pressurization of the intermediate vessel 210 such that the core column in the intermediate vessel 210 reaches a target pressure (e.g., a target reservoir pressure). In some embodiments, the intermediate vessel 210 may be provided with a pressure gauge 240 to detect its pressure. The example pressure pump 230 may be a hand-cranked pressure pump for ease of operational control.

In some embodiments, the intermediate vessel 210 may be connected to the saturated oil, allowing the core column to be submerged in the saturated oil.

In some embodiments, the intermediate vessel 210 may be connected to the fracturing fluid, allowing the core column to be immersed in the fracturing fluid.

In some embodiments, the intermediate vessel 210 may be connected to a drain line to drain the liquid therein.

In some embodiments, the intermediate vessel 210 may be connected to the above-described functional devices via a six-way valve 250, as shown in FIG. 2.

In some embodiments, the experimental equipment further includes an oven 260, and the intermediate vessel 210 may be placed in the oven 260 such that the intermediate vessel 210 and the core column therein reach a target temperature (e.g., a target reservoir temperature) under an action of the oven 260.

The example experimental process may include: lightly placing the core column into the intermediate vessel 210, connecting a pipeline between the vacuum pump 220 and the intermediate vessel 210, and checking that valves are all closed; turning on the vacuum pump 220, and opening the valves connecting the vacuum pump 220 and the intermediate vessel 210, vacuuming for 48 hours; after vacuuming, opening an inlet valve of the intermediate vessel 210 to allow the saturated oil to enter the intermediate vessel 210, closing the valve between the vacuum pump 220 and the intermediate vessel 210 after the saturated oil fills the entire the intermediate vessel 210, and then closing the inlet valve; pressurizing the intermediate vessel 210 to the target reservoir pressure with the pressure pump 230, closing all valves, removing the pipeline, and treating the saturated oil for 48 hours.

In S3, a CT scanning experiment may be performed on the core column after the saturated oil treatment, and an initial fracture porosity parameter of the core column combined with a digital core technology may be obtained.

The digital core technology is a reconstruction technology based on two-dimensional scanning electron microscope images or three-dimensional CT scan images, which uses computer image processing technology to complete digital core reconstruction through algorithms. A digital core reconstructed by the digital core technology may reflect a pore structure feature of the real core, thus obtaining an initial fracture porosity parameter of the core.

The initial fracture porosity parameter is a related parameter of the core column pore after the saturated oil treatment, such as one or more of initial fracture porosity, core permeability, or the like.

In some embodiments, in the operation S3, the core column may obtain the initial fracture porosity by the CT scanning device and the digital core technology.

In some embodiments, the CT scanning device may be communicatively connected to the system, which may control the CT scanning device to perform the CT scanning experiment. Based on the digital core technology, the system may process a result of the CT scanning experiment to obtain the initial fracture porosity.

In S4, the core column after the CT scanning experiment may be immersed into fracturing fluid at the temperature of the target reservoir and the pressure condition of the target reservoir, and a core mass increase amount of the core column may be tested at different immersion durations.

In some embodiments, the core column scanned by CT is wrapped with a rubber sleeve with high-temperature- and high-pressure-resistant on its sides, and then immersed in the fracturing fluid at the temperature and pressure condition of the target reservoir to test an increase amount of a core weight of the core column at different immersion durations. The example immersion durations may be 8 h, 12 h, 18 h, 24 h, or the like.

The fracturing fluid refers to a heterogeneous and unstable chemical system formed by mixing multiple additives in a certain proportion. It is the working fluid used for fracturing and transforming oil and gas layers. Its main function is to transmit the high pressure generated by ground equipment into the stratum, causing the stratum to rupture and form fractures, and transporting proppant along the fractures. In some embodiments, the fracturing fluid may be formulated according to a recipe used for on-site fracturing construction.

In some embodiments, in the operation S4, a rubber sleeve with high-temperature- and high-pressure-resistant is configured to wrap a side surface of the core column, and a circular interface at two ends of the core column are retained in contact with the fracturing fluid to prevent a prolonged high temperature and high pressure immersion causing the core column to break up and fall apart.

In some embodiments, the core column that has undergone the CT scanning experiment is immersed in the intermediate vessel filled with the fracturing fluid. Then, the pressure pump is configured to pressurize the intermediate vessel to reservoir pressure, all valves are closed, and the pipeline is removed. The entire intermediate vessel is then moved into an oven set to the reservoir temperature. The core immersed in the fracturing fluid is removed, surface liquid is wiped off, and it is weighed before conducting the CT scanning experiment. Before each soaking, the core column may be wrapped in a rubber sleeve, and after soaking, the rubber sleeve may be removed for weighing. Once the set experiment time is reached, the experiment is stopped.

In S5, the CT scanning experiment may be performed again on the core column immersed at different immersion durations, respectively, and an increased amount of fracture porosity may be obtained at different immersion durations combined within the digital core technology and the initial fracture porosity parameter, and a weight of newly added fracture porosity-fillable fracturing fluid may be calculated at different immersion durations.

The increased amount of fracture porosity is a parameter that measures the increase in fracture porosity of the core column after immersion. In some embodiments, the system may process a result of the CT scanning experiment based on the digital coring technology and compare result with the initial fracture porosity parameter to obtain the increased amount of fracture porosity.

A weight of the newly added fracture porosity-fillable fracturing fluid is a parameter configured to measure the weight of the fracturing fluid that may be filled in the new fractures added to the core column after soaking. In some embodiments, the system may calculate the weight of the newly added fracture porosity-fillable fracturing fluid based on a preset calculation process.

Exemplarily, an equation for calculating the weight of the newly added fracture porosity-fillable fracturing fluid in operation S5 is as follows:

$$\Delta m_{nf} = \Delta \Phi \times V \times \rho \tag{1}$$

wherein $\Delta m_{nf}$ refers to the weight of the newly added fracture porosity-fillable fracturing fluid, unit in g; $\Delta \Phi$ refers to an increased amount of fracture porosity, unit in %; V refers to a total volume of the core column, unit in cm$^3$; $\rho$ refers to a density of the fracturing fluid, unit in g/cm$^3$.

In S6, a curve of the core mass increase amount and a curve of the weight of the newly added fracture porosity-fillable fracturing fluid may be generated at different immersion durations, and an immersion time corresponding to an intersection of the two curves may be designated as an optimal soaking time.

The "soaking" refers to a process of shutting down the well after steam injection to allow steam to exchange heat with the reservoir rocks and fluids. In some embodiments, as the soaking time increases, the cumulative production increase amount may increase rapidly at first and then tend to stabilize at a certain value. A soaking time corresponding to an inflection point of the cumulative production increase amount is the optimal soaking time.

In some embodiments, the system may record and analyze experimental data, and plot the experimental data obtained from the aforementioned operations into charts. An oil-water displacement test may be performed through the saturated oil treatment to plot a curve showing a variation of a core weight with an immersion time. For example, the horizontal coordinate represents the immersion time, while the vertical coordinate represents the core mass increase amount. Through the CT scanning experiment, a curve may be plotted to show the variation of the fracture porosity with the immersion time. In this case, the horizontal coordinate represents the immersion time, while the vertical coordinate represents a weight of the newly added fracture porosity-fillable fracturing fluid. Through comprehensive analysis of the trends of the two curves, a time node corresponding to an intersection of the curve of the weight of the newly added fracture pore-fillable fracturing fluid and the curve of the core mass increase amount may be selected as the optimal soaking time.

In some embodiments, the core may be immersed in the fracturing fluid at the temperature and pressure condition of the reservoir. A hydration process causes an increase in a width of original fractures in the core and induces new fractures, resulting in an increase in fracture porosity and permeability. The fracturing fluid may enter the added fracture porosity and displace the crude oil in the initial pore space of the core under the effect of wettability and capillary forces, resulting in an increase in core weight. As the immersion time increases, if the core mass increase amount is less than the weight of the newly added fracture porosity-fillable fracturing fluid that may be filled in the new fracture porosity, it indicates that the effect of hydration permeability enhancement and oil-water replacement has reached the limit, and further soaking may lead to particle shedding, blocking the seepage channel of crude oil in the core. Therefore, the immersion time corresponding to the intersection of the curve of the core mass increase amount and the curve of the weight of the newly added fracture porosity-fillable fracturing fluid at different immersion durations may be selected as the optimal soaking time.

In S7, the operations S1-S6 may be performed on cores of a plurality of shale oil reservoirs to be evaluated for the production increase potential, respectively, a mass increase amount per volume unit of a core corresponding to the optimal soaking time for the cores in the operation S6 may be compared, and a mass increase amount per volume unit of the core may be ranked to determine the production increase potential corresponding to each of the plurality of shale oil reservoirs.

In some embodiments, in the operation S7, the greater the volume mass increase amount per unit of the core corresponding to the optimal soaking time is, the greater the increase in the production potential of the target reservoir corresponding to the core is.

For example, an equation for calculating the volume mass increase amount per unit of the core corresponding to the optimal soaking time for the cores is as follows:

$$\eta = \frac{\Delta m}{V} \tag{2}$$

wherein $\eta$ refers to the mass increase amount per volume unit of the core corresponding to the optimal soaking time, unit in g/cm$^3$; $\Delta m$ refers to a cumulative increase in weight of the core corresponding to the optimal soaking time, unit in g.

The process for evaluating the production potential described in the embodiments of the present disclosure is reliable in principle, highly operable, and accurate and overcomes the limitations of existing manners that rely solely on engineering experience and lack theoretical basis, resulting in relatively unstable application effects.

The oil-water replacement experiment in some embodiments of the present disclosure may be performed by placing the core column of the saturated crude oil under reservoir conditions, comprehensively considering the impacts of multiple factors such as hydration permeability enhancement and oil-water replacement, which is achieved by performing comprehensive analysis of the variation of core mass during the oil-water replacement experiment at different hydration times and the variation of core fracture porosity in the hydration permeability enhancement and CT scanning experiments, and the optimal soaking time may be determined by plotting the curve showing the core mass increase amount at different soaking times and the curve of the weight of the newly added fracture porosity-fillable fracturing fluid, the production potentials of different layers for production increase is evaluated by comparing the cumulative core increase amount per mass unit volume of cores at their respective optimal soaking time. This evaluation accurately assesses the production potential of multiple shale oil reservoirs and may guide the determination of the optimal soaking time.

Taking an example of a shale oil field in the East, the cores of two transformation target layers are selected for processing and treatment into standard core columns. Understandably, the following processing of the cores is based on the processed core columns. The processing treatment may be performed by system-controlled processing device. The two sets of reservoirs are at similar depths, and reservoir temperature and pressure conditions are basically the same, with a temperature of about 100° C. and a fluid pressure of about 20 MPa. The specific parameters of the cores finally obtained are as follows:

TABLE 1

Parameters of core specimens from different layers

| Reservoir | Core number | Diameter/ mm | Length/ mm | Mass/g | Core Volume/cm³ |
|---|---|---|---|---|---|
| No. 1 | 1# | 25 | 34.28 | 42.65 | 16.828 |
| No. 2 | 2# | 25 | 45.40 | 55.14 | 22.284 |

The following experimental operation may be performed through the system.

The specific operations include:

(1) placing a core to be used into an intermediate vessel for vacuum pumping and vacuum for 48 hours.

(2) opening an inlet valve on the top of the intermediate vessel to suck crude oil into the vessel, keeping the vacuum pump on. Once oil appears in a suction line, closing the inlet valve to ensure that the core is completely immersed.

(3) starting the pressure pump, remove air from the pipeline, connecting the pipeline to the inlet of the intermediate vessel, and pressurize it to 20 MPa using a hand pump. Then placing the intermediate vessel in a 100° C. oven for 48 hours for saturation.

(4) removing the rubber sleeve, quickly wiping off any oil on the surface, weighing it, and recording the data.

(5) performing a CT scanning on the saturated crude oil-treated core to observe the initial micro-crack morphology of the core and calculate the initial fracture porosity.

(6) preparing the fracturing fluid according to the equation used in on-site fracturing construction: water+0.1% drag reducer+0.05% flowback aid+0.2% anti-swelling agent.

(7) wrapping the CT-scanned core with a rubber sleeve with high-temperature- and high-pressure-resistant, immersing it in the intermediate vessel filled with fracturing fluid, starting the pressure pump, removing air from the pipeline, connecting the pipeline to the inlet of the intermediate vessel, and pressurize it to 20 MPa. Placing the intermediate vessel in a 100° C. oven and soaking the core in the fracturing fluid for 7 days at 100° C. and 20 MPa.

(8) removing the core after soaking for one cycle (7 days), removing the rubber sleeve, wiping off any floating liquid on the surface, weighing it, and performing the CT scanning experiment.

(9) repeating the operations (6) and (7) for a next cycle of core soaking and the CT scanning experiment.

(10) stopping the experiment when the designed experimental time is over.

(11) recording and analyzing the experimental data, plotting the curve of core mass increase amount with the soaking time, and using the equation (1) to calculate the mass increase amount of fracture porosity fillable fracturing fluid at different soaking times and plotting it as a curve.

(12) Comprehensively analyzing the trends of the two curves and select the time node corresponding to the intersection of the curve of the core mass increase amount and the curve of the newly added fracture porosity-fillable fracturing fluid mass as a suggested optimal soaking time.

(13) using the equation (2) to calculate the cumulative increase amount of the core mass per volume unit, sorting it, and determining the production potential of the reservoir where the core is located.

The experimental results are as follows:

TABLE 2

1# Changes in core mass and fracture porosity after immersing for different durations

| Immersion duration/ D | Core mass/ g | Fracture porosity/ % | core mass increase amount/ g | Fracture porosity increase amount/ % | Mass of newly added fracture porosity-fillable fracturing fluid/g |
|---|---|---|---|---|---|
| 0 | 42.982 | 0.14 | 0 | 0 | 0 |
| 7 | 43.212 | 0.29 | 0.23 | 0.15 | 0.025 |
| 14 | 43.227 | 0.35 | 0.015 | 0.06 | 0.010 |
| 21 | 43.228 | 0.38 | 0.001 | 0.03 | 0.005 |

TABLE 3

2# Changes in core mass and fracture porosity after immersing for different durations

| Immersion duration/D | Core mass/g | Fracture porosity/ % | core mass increase amount/g | Fracture porosity Increase amount/% | Mass of newly added fracture porosity-fillable fracturing fluid/g |
|---|---|---|---|---|---|
| 0 | 55.356 | 0.46 | 0 | 0 | 0 |
| 7 | 55.411 | 0.51 | 0.055 | 0.05 | 0.011 |
| 14 | 55.429 | 0.55 | 0.018 | 0.04 | 0.009 |
| 21 | 55.433 | 0.58 | 0.004 | 0.03 | 0.007 |

The experimental results in the above table indicate that the fracturing fluid may enter the fractures of the core under capillary action, the saturated formation oil within the core may be displaced. Due to a density difference between oil and water, the mass of the core increases. As the immersion duration increases, the core mass increase amount gradually decreases and tends to stabilize, and the mass increase amount of fracturing fluid that may be filled into the core fracture pores also slows down.

Figure 3:
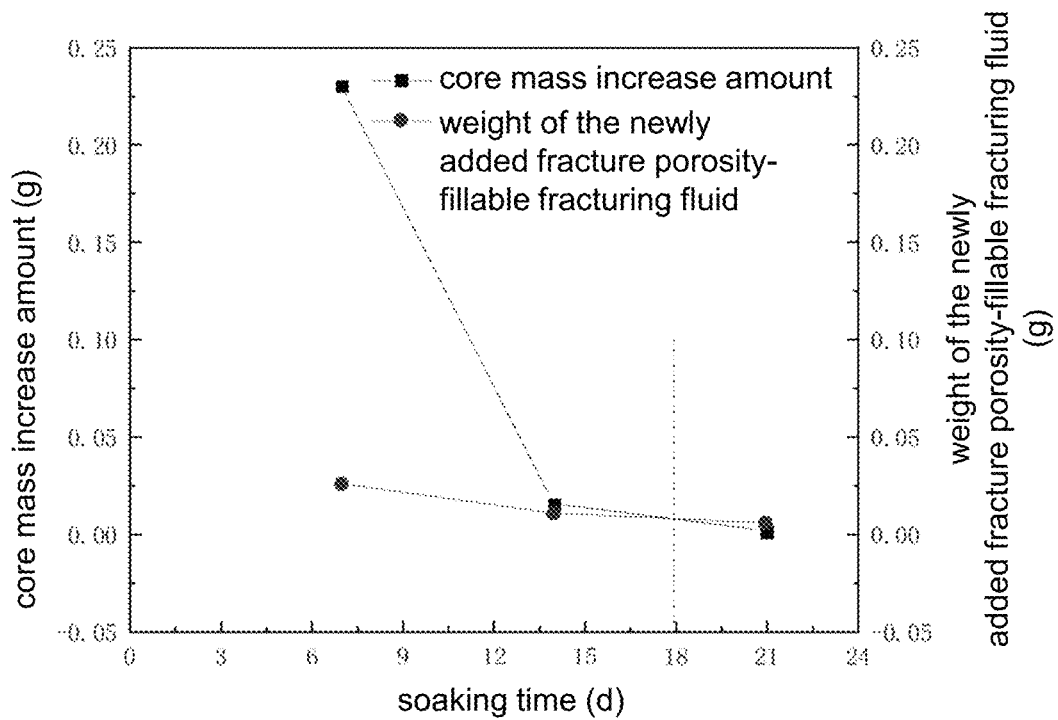
FIG. 3 is a curve diagram illustrating variation of core mass increase amount and mass increase amount of newly added fracture porosity-fillable fracturing fluid in a core with a soaking time for a Sample 1 # according to some embodiments of the present disclosure.

FIG. 3 is a curve diagram illustrating variation of core mass increase amount and mass increase amount of newly added fracture porosity-fillable fracturing fluid in a core with a soaking time for a Sample 1 #, according to some embodiments of the present disclosure.

Using data such as the mass, fracture porosity, core volume, and fracturing fluid density (1 g/cm³) of 1 # core at different immersion durations, these values are substituted into equation (1). The resulting data was plotted in FIG. 3. From FIG. 3, it can be seen that the intersection point of the curve representing the increase in mass of 1 # core and the curve representing the mass of fracturing fluid that may be filled into the core fracture pores corresponds to an immersion time of 18 days. Therefore, 18 days was chosen as the optimal soaking time for 1 # core.

Figure 4:
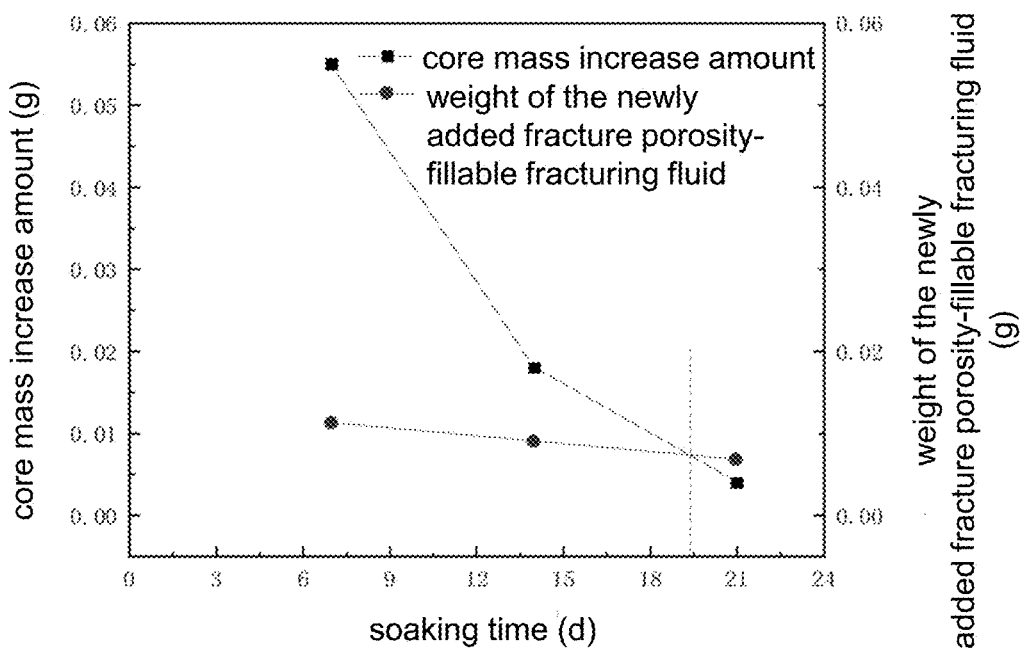
FIG. 4 is a curve diagram illustrating variation of core mass increase amount and mass increase amount of newly added fracture porosity-fillable fracturing fluid in a core with a soaking time for a Sample 2 # according to some embodiments of the present disclosure.

FIG. 4 is a curve diagram illustrating the variation of core mass increase amount and mass increase amount of newly added fracture porosity-fillable fracturing fluid in a core with a soaking time for a Sample 2 # according to some embodiments of the present disclosure.

Similarly, the data calculated from 2 # core may be plotted in FIG. 4, and from FIG. 4, it may be determined that the optimal soaking time for 2 # core is 19 days.

Figure 5:
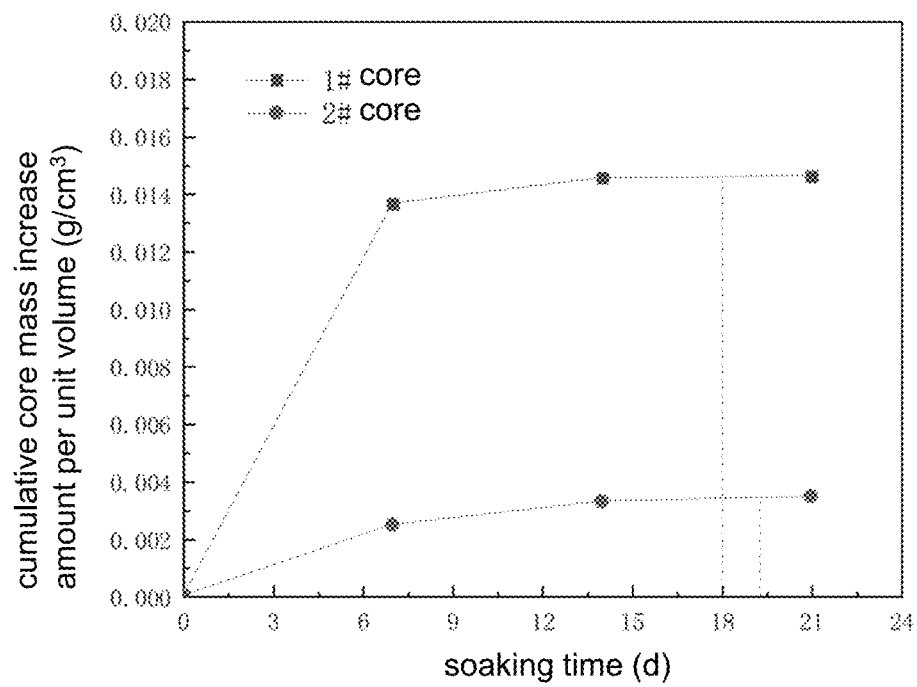
FIG. 5 is a curve diagram illustrating variation of cumulative core mass increase amount per unit volume of cores with a soaking time for Samples 1 # and 2 # according to some embodiments of the present disclosure.

FIG. 5 is a curve diagram illustrating variation of cumulative core mass increase amount per volume unit of cores with a soaking time for Samples 1 # and 2 # according to some embodiments of the present disclosure.

The curve showing the cumulative mass increase amount per volume unit of the two cores over soaking time is plotted in FIG. 5. Comparing the cumulative mass increase amount per volume unit of the two cores at their respective optimal soaking times, it can be seen that the layer where 1 # core is located has greater potential for increasing production.

The basic concepts have been described above, apparently, in detail, as will be described above, and does not constitute limitations of the disclosure. Although there is no clear explanation here, those skilled in the art may make various modifications, improvements, and modifications of present disclosure. This type of modification, improvement, and corrections are recommended in present disclosure, so the modification, improvement, and the amendment remain in the spirit and scope of the exemplary embodiment of the present disclosure.

At the same time, present disclosure uses specific words to describe the embodiments of the present disclosure. As "one embodiment", "an embodiment", and/or "some embodiments" means a certain feature, structure, or characteristic of at least one embodiment of the present disclosure. Therefore, it is emphasized and should be appreciated that two or more references to "an embodiment" or "one embodiment" or "an alternative embodiment" in various parts of present disclosure are not necessarily all referring to the same embodiment. Further, certain features, structures, or features of one or more embodiments of the present disclosure may be combined.

In addition, unless clearly stated in the claims, the order of processing elements and sequences, the use of numbers and letters, or the use of other names in the present disclosure are not used to limit the order of the procedures and methods of the present disclosure. Although the above disclosure discusses through various examples what is currently considered to be multiple useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially". Unless otherwise stated, "about," "approximate," or "substantially" may indicate ±20% variation of the value it describes. Accordingly, in some embodiments, the numerical parameters used in the specification and claims are approximate values, and the approximation may change according to the characteristics required by the individual embodiments. In some embodiments, the numerical parameter should consider the prescribed effective digits and adopt a general digit retention method. Although in some embodiments, the numerical fields and parameters used to confirm the breadth of its range are approximate values, in specific embodiments, such numerical values are set as accurately as possible within the feasible range.

With respect to each patent, patent application, patent application disclosure, and other material cited in the present disclosure, such as articles, books, manuals, publications, documents, etc., the entire contents thereof are hereby incorporated by reference into the present disclosure. Application history documents that are inconsistent with the contents of the present disclosure or that create conflicts are excluded, as are documents (currently or hereafter appended to the present disclosure) that limit the broadest scope of the claims of the present disclosure. It should be noted that in the event of any inconsistency or conflict between the descriptions, definitions, and/or use of terms in the materials appended to the present disclosure and those described in the present disclosure, the descriptions, definitions, and/or use of terms in the present disclosure shall prevail.

At last, it should be understood that the embodiments described in the present disclosure are merely illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A method for evaluating a production potential for volume fracturing of a shale oil reservoir and determining a soaking time, comprising:
S1, obtaining an underground core of a target reservoir, cleaning the underground core and processing the underground core into a core column, wherein two end surfaces of the core column are kept flat;
S2, performing a saturated oil treatment on the core column in the step 1 at a temperature of the target reservoir and a pressure condition of the target reservoir;
S3, performing a CT scanning experiment on the core column after the saturated oil treatment, and obtaining an initial fracture porosity parameter of the core combined with a digital core technology;
S4, immersing the core column after an initial CT scanning experiment into fracturing fluid at the temperature of the target reservoir and the pressure condition of the target reservoir, and testing a core mass increase amount of the core column at different immersion durations;
S5, performing the CT scanning experiment again on the core column immersed at different immersion durations, respectively, obtaining an increased amount of fracture porosity at different immersion durations combined within the digital core technology and the core initial fracture porosity parameter, and calculating a weight of newly added fracture porosity-fillable fracturing fluid at different immersion durations;
S6, drawing a curve of the core mass increase amount and a curve of the weight of the newly added fracture porosity-fillable fracturing fluid at different immersion durations, and designating an immersion time corresponding to an intersection of the two curves as an optimal soaking time;
S7, performing the operations S1-S6 on cores of a plurality of shale oil reservoirs to be evaluated for the production increase potential, respectively, comparing a mass increase amount per volume unit of a core corresponding to the optimal soaking time for the cores in the operation S6, and ranking a mass increase amount per volume unit of the core to determine the production increase potential corresponding to each of the plurality of shale oil reservoirs;
wherein in the operation S2, a vacuum treatment is performed on the core column, a duration of the vacuum treatment is not less than 48 h, a temperature and a pressure condition of the saturated oil is the same as the temperature and the pressure condition of the target reservoir during the saturated oil treatment, and for ensuring that an intermediate vessel is completely filled with the saturated oil, the duration of the saturated oil treatment is not less than 48 h;
in the operation S5, an equation for calculating the weight of the newly added fracture porosity-fillable fracturing fluid is as follow:

$$\Delta m_{nf} = \Delta \Phi \times V \times \rho$$

wherein $\Delta m_{nf}$ refers to the weight of the newly added fracture porosity-fillable fracturing fluid, unit in g; $\Delta \Phi$ refers to an increased amount of fracture porosity, unit in %; V refers to a total volume of the core column, unit in cm$^3$; $\rho$ refers to a density of the fracturing fluid, unit in g/cm$^3$;
in the operation S7, the greater the mass increase amount per volume unit of the core corresponding to the optimal soaking time is, the greater the increase in the production increase potential of the target reservoir corresponding to the core is, a calculation equation is as follow:

$$\eta = \frac{\Delta m}{V}$$

wherein $\eta$ refers to the mass increase amount per volume unit of the core corresponding to the optimal soaking time, unit in g/cm$^3$; $\Delta m$ refers to a cumulative increase in weight of the core corresponding to the optimal soaking time, unit in g.

2. The method of claim 1, wherein in the operation S1, the core column is a standard column, upper and lower end surfaces of the core column are kept flat, the method further includes:
numbering the core column and recording a dimension, a weight, and a volumetric parameter of the core column.

3. The method of claim 1, wherein the method further includes:
in the operation S3, obtaining the initial fracture porosity based on the CT scanning experiment and the digital core technology.

4. The method of claim 1, wherein in the operation S4, a rubber sleeve with high-temperature- and high-pressure-resistant is configured to wrap a side surface of the core column, and a circular interface at two ends of the core column are retained in contact with the fracturing fluid to prevent a prolonged high temperature and high pressure immersion causing the core column to break up and fall apart.

* * * * *